(12) United States Patent
Beaurepaire et al.

(10) Patent No.: US 8,227,767 B2
(45) Date of Patent: Jul. 24, 2012

(54) COHERENT NONLINEAR MICROSCOPY SYSTEM AND METHOD WITH VARIATION OF THE FOCAL VOLUME IN ORDER TO PROBE THE NANOSTRUCTURE OF ORGANIZED MATERIALS

(75) Inventors: Emmanuel Jean-Marc Beaurepaire, Palaiseau (FR); Nicolas Olivier, Paris (FR); Delphine Debarre, Paris (FR); Marie-Claire Schanne-Klein, Verrieres le Buisson (FR); Jean-Louis Martin, Bures sur Yvette (FR)

(73) Assignee: Ecole Polytechnique, Palaiseau (FR)

( * ) Notice: Subject to any disclaimer, the term of this patent is extended or adjusted under 35 U.S.C. 154(b) by 3 days.

(21) Appl. No.: 13/001,258

(22) PCT Filed: Jun. 26, 2009

(86) PCT No.: PCT/FR2009/051236
§ 371 (c)(1), (2), (4) Date: Mar. 14, 2011

(87) PCT Pub. No.: WO2009/156702
PCT Pub. Date: Dec. 30, 2009

(65) Prior Publication Data
US 2011/0147616 A1    Jun. 23, 2011

(30) Foreign Application Priority Data
Jun. 27, 2008 (FR) .................................... 08 54347

(51) Int. Cl.
*G01N 21/64* (2006.01)

(52) U.S. Cl. .................................................. 250/459.1
(58) Field of Classification Search ............... 250/459.1
See application file for complete search history.

(56) References Cited

U.S. PATENT DOCUMENTS

| | | | | |
|---|---|---|---|---|
| 5,576,550 A | * | 11/1996 | Koppikar | 250/459.1 |
| 2006/0017001 A1 | | 1/2006 | Donders et al. | |
| 2006/0051878 A1 | * | 3/2006 | Dickson et al. | 436/518 |
| 2008/0118912 A1 | * | 5/2008 | Dickson et al. | 435/6 |

FOREIGN PATENT DOCUMENTS

| | | |
|---|---|---|
| CA | 2267431 A1 | 2/1999 |
| DE | 19733193 A1 | 2/1999 |
| EP | 1617206 A | 1/2006 |

OTHER PUBLICATIONS

Gersen et al., "Near-field effects in single molecule emission," 2001, Journal of Microscopy, vol. 202, pp. 374-378.*

(Continued)

*Primary Examiner* — Kiho Kim
(74) *Attorney, Agent, or Firm* — Young & Thompson

(57) ABSTRACT

A method for the dimensional characterization of a structured material, in which method: an excitation laser beam suitable for coherent nonlinear microscopy is generated, this excitation laser beam being focused in a focal volume within the structured material; signals emitted by the structured material are detected; a plurality of emission patterns, each corresponding to one particular shape of the focal volume, is produced, the particular shapes being obtained for various non-Gaussian spatial profiles of the excitation laser beam wavefront; and on the basis of the emission patterns thus produced, dimensional characteristics of the structured material are deduced therefrom.

27 Claims, 3 Drawing Sheets

OTHER PUBLICATIONS

Yew et al, "Second harmonic generation polarization microscopy with tightly focused linearly and radially polarized beams", Optics Communications, 2007, pp. 453-457, vol. 275.

Krishnamacheri et al., "Imaging chemical interfaces perpendicular to the optical axis with focus-engineered coherent anti-Stokes Raman scattering microscopy", Chemical Physics, Nov. 15, 2007, pp. 81-88, vol. 341.

French Search Report, Dated Feb. 20, 2009, in FR 0854347/FA708991.

* cited by examiner

COHERENT NONLINEAR MICROSCOPY SYSTEM AND METHOD WITH VARIATION OF THE FOCAL VOLUME IN ORDER TO PROBE THE NANOSTRUCTURE OF ORGANIZED MATERIALS

The present invention relates to a coherent nonlinear microscopy method for characterizing a structured material. It also relates to a system implementing such a method.

It has a particularly advantageous application in the field of the characterization of structured artificial or biological materials such as: ordered arrangements of collagen (cornea, bone, etc), muscular fibres, biomineral structures, etc. The present invention can in particular be used in the context of the diagnosis of defects in nanomaterials or of pathologies characterized by the disorganization of such materials.

In the prior art, in order to probe the structure of thick materials organized on the nanometric scale (20 nm-1 µm), use has been made of approaches such as electron microscopy, X-ray diffusion, or atomic force microscopy, which impose constraints in the preparation and geometry of the samples, and which in particular are not compatible with the study of living biological tissues.

Nonlinear optical microscopy of organized structures is also known. It has been shown that certain organized structures can be detected in nonlinear microscopy. In particular, SHG (Second Harmonic Generation) microscopy makes it possible to detect fibrillar collagen, muscle fibres, etc. However, the current approach of the prior art does not give access to the parameters of structures (periodicity, order parameters) on the sub-micrometric scale.

Moreover, nonlinear microscopy with modulation of focal volume is also known. At present, two applications of coherent nonlinear microscopy with modulation of the focal volume have been proposed:

the document by Yew et al., "Second harmonic generation polarization microscopy with tightly focused linearly and radially polarized beams", E. Y. S. Yew & C. J. R. Sheppard, Optics Commun. 275, 453 (2007), describes a microscopy making it possible to create a focal volume with a strong axial polarization using SHG microscopy for detecting a fibre of collagen axially oriented, to the extent where generally a collagen fibre in this orientation gives little signal;

the document by Krishnamachari et al., "Imaging chemical interfaces perpendicular to the optical axis with focus-engineered coherent anti-Stokes Raman scattering microscopy", V. V. Krishnamachari & E. O. Potma, Chemical Physics (2007), describes a method for creating an antisymmetric focal volume making it possible to "suppress" a homogeneous background in CARS microscopy, in order to make the small objects and interfaces stand out. The documents by Yew and Krishnamachari do not describe a method aimed at obtaining information on sub-micrometric structure.

An objective of the present invention is to measure sub-micronic parameters of a structured material in a non-invasive manner. Another objective of the invention is the three-dimensional measurement of the structure of a material. Yet another objective of the present invention is a non-complex method for characterizing a structured material.

At least one of said objectives is achieved with a method for the dimensional characterization of a structured material, in which method:

an excitation laser beam suitable for coherent nonlinear microscopy is generated, the wavefront of which has a spatial profile which is shaped (intensity, phase, polarization) by a modulation device; this excitation laser beam being focussed in a focal volume within the structured material;

signals emitted by the structured material are detected;

a plurality of emission patterns, each one corresponding to a particular shape of the focal volume, is produced; the particular shapes being obtained for various non-Gaussian spatial profiles of the excitation laser beam wavefront; and dimensional characteristics of said structured material are deduced from the emission patterns thus produced.

The present invention is a new optical method for the non-destructive characterization of three-dimensional structured biological or artificial materials and providing a coherent non-linear microscopy signal on scales ranging from a few tens to a few hundreds of nanometres. The present invention goes against a generally accepted prejudice according to which, in optical microscopy, the measurement of nanometric distances is almost impossible. Until now, electron scanning microscopy or X-rays have been used instead. The excitation laser beam according to the invention is generally a train of picosecond or femtosecond pulses.

With the method according to the invention, the nanometric structure of the structured material is probed, moreover in a non-invasive manner. The excitation laser beam can advantageously be focussed in the structured material in situ, it can also be done in vivo, which is not the case for most of the methods of the prior art.

Moreover, the alternative methods of the prior art are either limited to two dimensions (Atomic Force Microscopy AFM), or are based on shorter wavelength radiations (electron microscopy, X-rays). They are much more restrictive in terms of sample preparation, and in particular do not apply to three-dimensional imaging of intact biological tissues, thick samples or hydrated media. On the contrary, the present invention can advantageously be applied for example to the diagnosis of the state of organisation of biomaterials (cornea, etc.) or of nanostructured materials, in situ, in three dimensions, and without preparation. In particular, the method according to the invention is compatible with aqueous and thick samples.

With respect to the YEW document, the method according to the present invention uses a different non-Gaussian spatial profile for each measurement. The series of emission patterns produced makes it possible to deduce the structural characteristics of the observed material therefrom.

By way of non-limiting example, the dimensional or structural characteristics include at least one item from the following group: periodicity, distance and angle. A person skilled in the art will easily understand that other characteristics can be determined depending on the observed materials and the spatial profiles used.

According to an advantageous feature of the invention, the various spatial profiles include radially symmetric concentric phase profiles, which can be of the Laguerre-Gaussian, Bessel or "bottle beam" type for example.

Other types of spatial profiles can be used, in particular radially antisymmetric phase profiles, such as for example of the Hermite-Gaussian type.

Each profile is obtained by a shaping of the wavefront, in phase and/or in intensity, of the excitation laser beam. In practice, a spatial light modulator can be used. By way of non-limiting example this spatial light modulator can be:

a phase plate or several phase plates which are placed on a rotary wheel; each plate corresponding to a predetermined shaping; in this way several emission patterns are produced for the various phase plates;

a liquid crystal matrix;
a deformable mirror; or
a combination thereof.

In other words, each focal volume corresponds to a given spatial profile which is obtained by modifying the phase of the excitation laser beam and/or by modifying the intensity of the excitation laser beam. Moreover, it is also possible to modify the polarization of the excitation laser beam in order to have a larger number of variables in the emission patterns. Similarly, it is also possible to produce different emission patterns for different wavelengths.

According to an advantageous characteristic of the invention, a detection pattern is generated from signals emitted backwards by the structured material. In other words, it is a matter of epidetection. The backward emission can result either from the shaping of the focal volume or from the backscattering of a portion of the radiation by the thick material.

It is also possible to produce a detection pattern from transmission signals emerging downstream of the structured material, i.e. the signals that are not backscattered by the structured material. Generally, forward emission refers to transmission and backward emission refers to backscattering. Advantageously, with the method according to the invention, the spatial profile can be modified in such a way as to affect the forward/backward emission ratio and effectively to enhance the analysis of the emission patterns. More precisely, it is possible to determine a forward/backward emission efficiency which is then used as a comparison criterion during the deduction of the dimensional characteristics. In particular, for a same spatial profile, a detection of both backscattered signals and transmitted signals of the structured material can be carried out.

For the detection of the signals emitted by the structured material, it is possible to use a detector of the one-point type with or without a spatial filter or, in general, a camera. In this latter case, the whole of the signal coming from the structured material is picked up without preference being given to any particular direction.

According to an advantageous embodiment of the invention, deduction of the dimensional characteristics is carried out by comparing the emission patterns thus produced with predetermined digital models. These digital models can be obtained during a calibration stage using a "control" structured material the dimensional characteristics of which are known.

According to a variant of the invention, an excitation laser beam is scanned over or in the structured material.

According to another aspect of the invention, a system for the dimensional characterization of a structured material is proposed for implementing the method as described above. This system comprises:

a laser source laser able to generate an excitation laser beam suitable for coherent nonlinear microscopy;
a spatial light modulator for modifying the spatial profile of the wavefront of the excitation laser beam into a non-Gaussian spatial profile;
a lens for focussing this excitation laser beam in a focal volume within the structured material;
a detector for detecting signals emitted by the structured material; and
a processing unit for producing a plurality of emission patterns each one corresponding to a particular shape of the focal volume; the particular shapes being obtained for different non-Gaussian spatial profiles of the wavefront of the excitation laser beam; and for deducing dimensional characteristics of said structured material from the emission patterns thus produced.

Advantageously, the detector is arranged in such a way as to detect the signals emitted backwards, or backscattered, by the structured material. This detector can also be arranged in such a way as to detect the transmission signals emerging downstream of the structured material. Preferably, the system comprises a scanning device for making the laser beam scan over or in the structured material.

Other advantages and features of the invention will become apparent on examining the detailed description of an embodiment that is in no way limiting and the appended drawings, in which.

Figure 1:
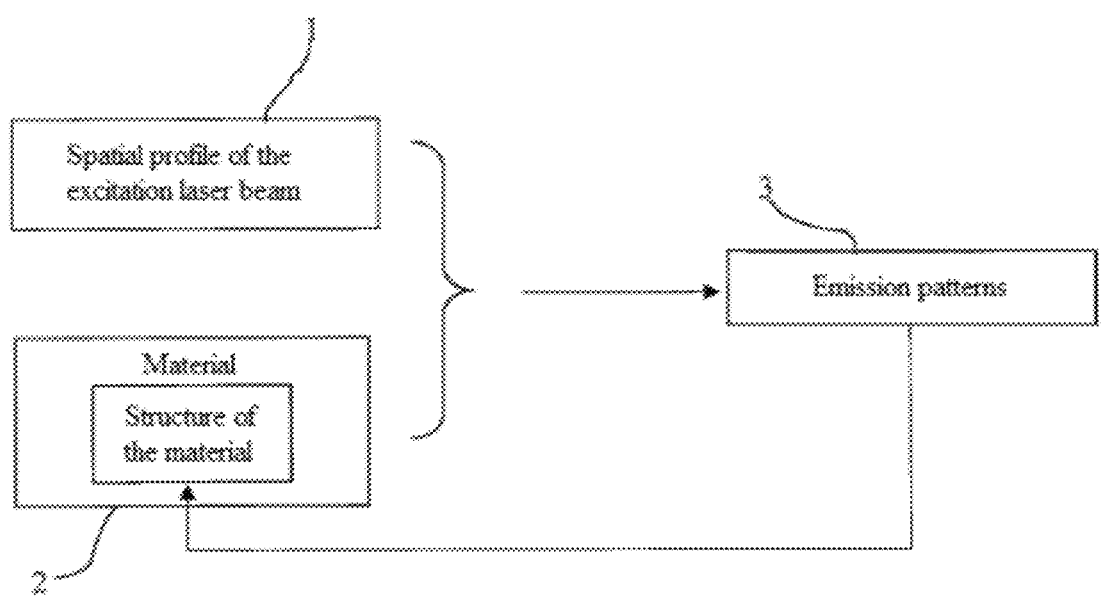
FIG. 1 is a simplified view showing three constitutive parameters of the invention.
Figure 7:
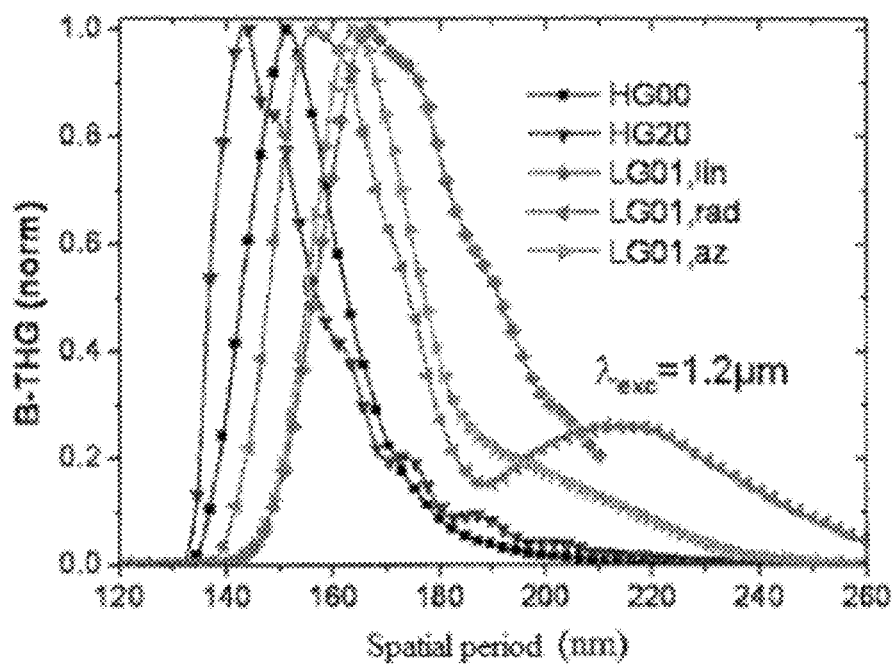
Figure 8:
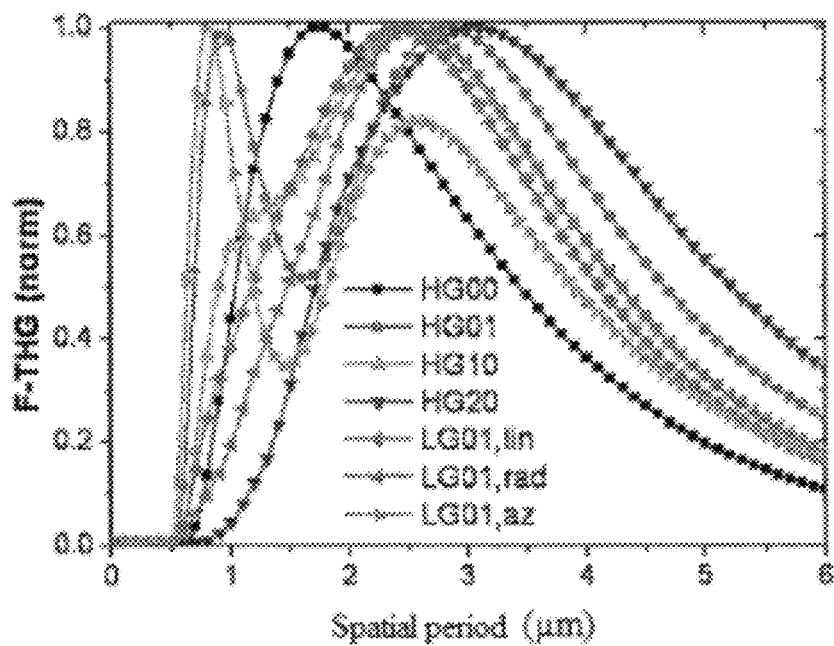

FIG. 7 is a graph showing the backward THG (Third Harmonic Generation) emission efficiency of a nanostructured material probed with different excitation profiles, as a function of the characteristic size of the material; and FIG. 8 is a graph showing the forward THG (Third Harmonic Generation) emission efficiency of a microstructured material probed with different excitation profiles, as a function of the characteristic size of the material;

The principle of implementing the method according to the invention is shown in FIG. 1. Three parameters are shown, one in each of three blocks. The parameter 1 "spatial profile of the excitation laser beam" is in fact a variable that can be modified. The parameter 2 "structure of the material" is the parameter to be characterized and which is therefore present in the material but is unknown. The parameter 3 "emission patterns" is data from which the parameter 2 "structure of the material" is deduced. Ideally, several emission patterns for different spatial profiles are produced and then these emission patterns are compared with predetermined digital models.

The present invention uses, in addition to other features, coherent nonlinear microscopy with modulation of focal volume for probing a nanometric structure of a material by means of non-Gaussian spatial profiles.

Figure 2:
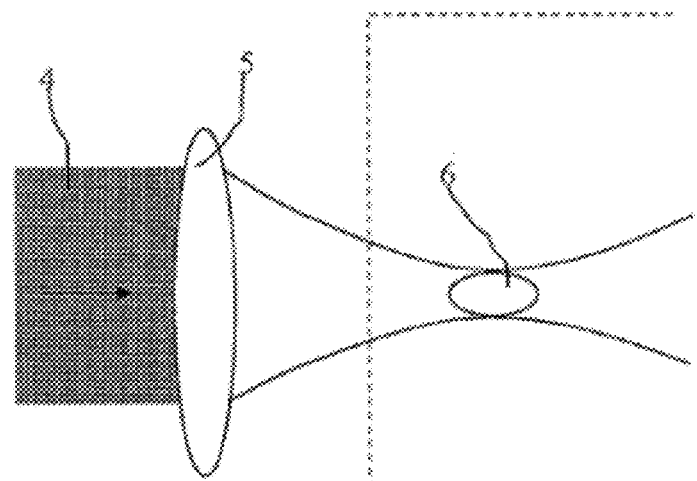
FIG. 2 is a simplified view showing a focal volume in a structured material.

In general, coherent nonlinear microscopy makes it possible to obtain images of polarizable materials having a non-linear non-zero second order or third order susceptibility. The contrast mechanism is based on the interaction between a train of focussed pulses (femtosecond or picosecond laser) and the observed medium, in a confined volume confine in the vicinity of the focussing point of the laser. In FIG. 2, there can be seen a laser beam 4 that is focussed by means of a lens 5 in a focal volume 6 within a structured material 7. This focal volume 6 can have the shape of an ovoid of width 1.5 μm and of height 0.4 μm for example. An image is then produced by scanning the focussing point in two or three dimensions. The usable optical effects comprise in particular second harmonic generation (SHG), third harmonic generation (THG), Coherent Anti-Stokes Raman Scattering (CARS), Sum Frequency Generation (SFG), Difference Frequency Generation (DFG), Impulsive Stimulated Raman Scattering (ISRS), Coherent Stokes Raman Scattering (CSRS), etc. In this type of microscopy, the detected signal is the coherent superimposition at the level of the detector of the waves radiated by the induced dipoles within the excitation volume.

Figure 3:
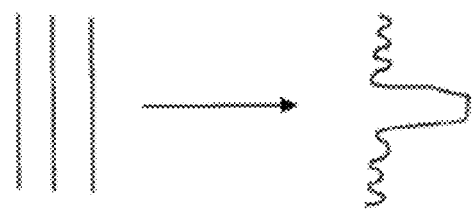
FIG. 3 is a simplified view showing the conversion of a wavefront.

The objective of the present invention is to produce several emission patterns by modifying the spatial profile excitation laser beam 4. FIG. 3 shows an example of modification of plane profile into a given profile. The given profile is chosen because it is known from experience or by calibration in particular that such a profile makes it possible to highlight certain dimensional characteristics of the observed material. The present invention is thus noteworthy by the fact that the variation of the spatial profile of the laser beam modifies the emission pattern; these modifications being linked to the nanometric characteristics of the structured material.

Figure 4:
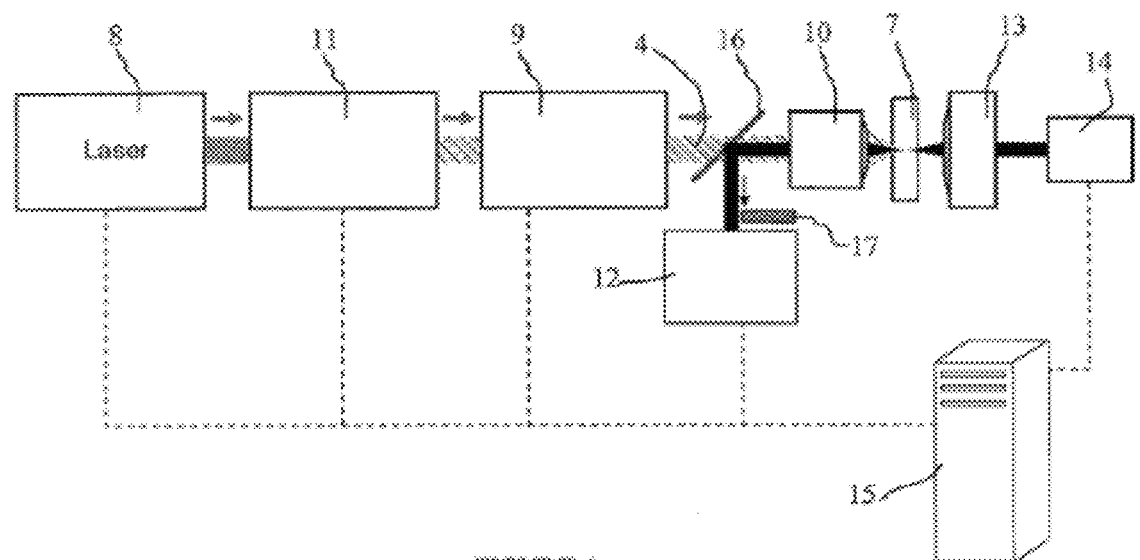
FIG. 4 is a block diagram of a system according to the invention.

FIG. 4 describes a system according to the invention for characterizing the structured material. This system comprises a nonlinear microscope composed of:
- a pulsed laser source 8 suitable for linear microscopy, i.e. an emission of a train of picosecond or femtosecond pulses at a high rate or emission of one or two beams of tunable central wavelength;
- a device 9 for scanning with the excitation beam 4; alternatively, this scanning device can be replaced by a device for scanning (not shown) with the structured material 7, in this case the excitation laser beam can remain fixed; and
- a lens 10 for focussing the excitation laser beam 4 in the structured material 7.

The system also advantageously comprises a spatial light modulator 11 for the spatial shaping of the wavefront of the excitation laser beam 4. This spatial light modulator can be a phase modulator and possibly an amplitude (intensity) modulator.

The system also comprises a detector 12 of the one-point or spatially resolved type for detecting the light (signal) emitted by the structured material 7 and collected by the lens 10 via a separator 16. A condenser 13 and a second detector 14 constitute a second optional detection path making it possible to detect the light emitted in another direction, if the geometry of the structured material is appropriate for this. For certain applications, the two detection paths can be used simultaneously. A processing unit 15 connected in particular to the laser source 8, to the spatial light modulator 11, to the scanning device 9 and to the detectors 12 and 14, makes it possible to control these different elements to which it is connected, to retrieve emission patterns and to deduce from them the structural characteristics of the structured material 7.

The system shown in FIG. 4 therefore combines in particular a nonlinear microscopy system comprising a scanning microscope and a femtosecond laser with tunable wavelength in particular, with a device for the spatial shaping of the wavefront with, moreover, the production of a plurality of emission patterns for different non-Gaussian spatial shapes of the wavefront, and this in order to deduce from said emission patterns, structural characteristics of a material.

With coherent nonlinear microscopy (Second Harmonic Generation (SHG) microscopy, Third Harmonic Generation (THG) microscopy, CARS microscopy, etc.), the light which is detected in order to form the image is emitted in directions which are determined, on the one hand, by the geometry of the structured material 7 on the sub-micrometric scale and, on the other hand, by the distribution of the light field in the vicinity of the focus of the lens 10. Conventionally, the excitation beam is a Gaussian beam and the emission generally takes place in the direction of propagation of this beam. However, in the present invention, the angles of emission and/or the directions of emission, in particular the forward/backward ratio, as well as the emission intensity, are modified by modifying the distribution of the field at the focus of the lens by using a non-Gaussian beam. This can be carried out by controlling the spatial profile of the beam at the input to the lens 10 using the spatial light modulator 11. In the case of an organized material having a nanometric structure repeated in an almost periodic manner on length of the order of one micrometre, the recording by the processing unit 15 of several signals or emission patterns obtained with different beam shapes makes it possible to deduce the characteristic lengths or the order parameters of the structured material 7, on a scale smaller than the wavelength. In fact, the signal intensity emitted in a given direction, for example backwards, will depend on the spatial profile of the excitation and on the distribution of the characteristic lengths to be probed.

In imaging with such a system according to the invention the processing time per pixel can be a few µs.

Figure 5:
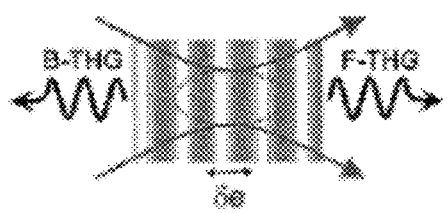
FIG. 5 is a simplified view showing backscattered and transmitted signals.

With the system according to the invention, the three-dimensional distribution of the excitation field in the focal volume is therefore controlled by the intensity, the phase and optionally the polarization; the constructive or destructive interference phenomena making it possible to prioritize emission in a particular direction, for example backward rather than forward. FIG. 5 shows the focal volume 6, in the vicinity of the focussing point of the excitation beam 4, within the structured material 7 of characteristic period $\delta e$. The B-THG (Backward-THG) signal represents the THG (Third Harmonic Generation) backward emission, i.e. an epidetection which can be detected by the detector 12. The F-THG (Forward-THG) signal represents the THG (Third Harmonic Generation) forward emission, i.e. an emission which can be detected by the second detector 14.

Figure 6:
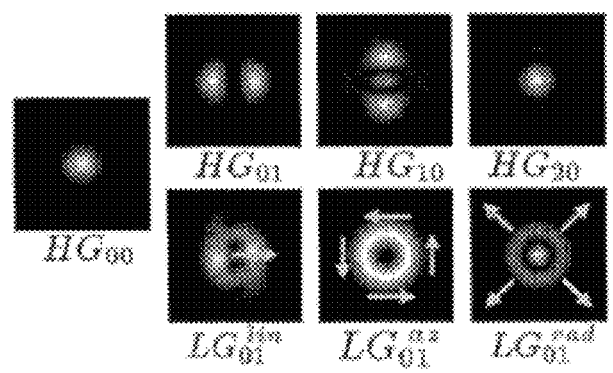
FIG. 6 is a view showing different types of spatial profiles.

In the case of a material having a periodic structure extending over about two microns along the optical axis, the forward/backward emission efficiency strongly depends on the axial distribution of the excitation field within the focal volume. As has been seen, this distribution can be controlled by modifying the spatial profile of the excitation laser beam upstream of the lens 10. In particular, it is possible to use radially symmetric concentric phase profiles such as the Laguerre-Gaussian, Bessel, "bottle beam", etc. FIG. 6 shows three examples of phase profiles of the Laguerre-Gaussian type: $LG_{01}^{lin}$, $LG_{02}^{as}$, $LG_{03}^{rad}$. By recording the signal or its spatial emission profile for several shapes of the excitation laser beam 4, it is thus possible to measure a periodicity or an order parameter of the structured material 7.

Similarly, for a material having a sub-micrometric lateral structure (interface or periodic medium), the direction and the efficiency of the emission are controlled by the lateral structure of the focal volume, which can be modified by using a beam profile breaking the radial symmetry such as the Hermite-Gaussian, or other profile. FIG. 6 shows four examples of phase profiles of the Hermite-Gaussian type: $HG_{00} HG_{03} HG_{10} HG_{20}$ It is thus possible to deduce lateral characteristic magnitudes such as the periodicity, the distance, and the angle, on a sub-micrometric scale, by recording the emission pattern for several shapes of the excitation volume. Depending on the constraints associated with the structured material 7, the measurement can be made either by epidetection on a one-point detector such as the detector 12 for example possibly with a spatial filter 17 as in FIG. 4; or by epidetection on an imager, a camera (not shown); or by combining epidetection and detection in transmission (detectors 12 and 14).

FIGS. 7 and 8 show emission efficiencies as a function of the characteristic length of a periodic material, for each spatial profile as shown in FIG. 6. These emission efficiencies illustrate the sensitivity of the emission to the shape of the focal volume, for a structured material oriented along the optical axis. These diagrams correspond to a backward THG (B-THG) and forward THG (F-THG) emission by a periodic structure excited at 1200 nm. The measurement of these signals emitted for different spatial shapings makes it possible to characterize the characteristic lengths in the range 140-240 nm and 0.7-7 µm. Other periodicities can be probed by changing the excitation wavelength, for example 600 to 1600 nm, and the shape of the excitation beam: Laguerre-Gaussian, Bessel, radially symmetric concentric phase profiles, in particular "bottle beam", etc.

The invention therefore relates to an optical method for characterization of structured materials, providing a coherent nonlinear microscopy signal, at scales ranging from a few tens to a few hundred nanometres. It advantageously applies to applications relating to the characterization of artificial or biological structured materials. In particular, such applications include:

- the characterization of ordered arrangements of collagen: cornea, bone etc.,
- the characterization of muscular structures,
- the characterization of biomineral structures: biocrystals, spicules, etc.,
- the diagnosis of pathologies characterized by a disorganization in these types of structures, such as: dystrophy of the cornea, oedema, muscular dystrophy etc.,
- the characterization of thin-layered materials,
- the characterization of microcavities, nanostructured materials, etc. and
- the characterization of the metamaterials.

Of course, the invention is not limited to the examples which have just been described and numerous adjustments can be made to these examples without exceeding the scope of the invention.

The invention claimed is:

1. Method for the dimensional characterization of a structured material, in which method:
   - an excitation laser beam suitable for coherent nonlinear microscopy is generated the wavefront of which has a spatial profile which is shaped by a modulation device; this excitation laser beam being focussed in a focal volume within the structured material;
   - signals emitted by the structured material are detected;
   - a plurality of emission patterns, each one corresponding to a particular shape of the focal volume, is produced; the particular shapes being obtained for various non-Gaussian spatial profiles of the excitation laser beam wavefront; and
   - dimensional characteristics of said structured material are deduced from the emission patterns thus produced.

2. Method according to claim 1, characterized in that the spatial profile is modified by modifying the phase of the excitation laser beam.

3. Method according to claim 1, characterized in that the spatial profile is modified by modifying the intensity of the excitation laser beam.

4. Method according to claim 1, characterized in that the spatial profile is modified by modifying the polarization of the excitation laser beam.

5. Method according to claim 1, characterized in that a detection pattern is produced from signals emitted backwards, or backscattered, by the structured material.

6. Method according to claim 1, characterized in that a detection pattern is produced from transmission signals emerging downstream of the structured material.

7. Method according to claim 1, characterized in that, for a same spatial profile, detection of both backward emitted or backscattered signals and transmitted signals of the structured material is carried out.

8. Method according to claim 1, characterized in that a forward/backward emission efficiency is determined, which is then used as a comparison criterion during the deduction of the dimensional characteristics.

9. Method according to claim 1, characterized in that the deduction of the dimensional characteristics is carried out by comparing the emission patterns thus produced with predetermined digital models.

10. Method according to claim 1, characterized in that the different spatial profiles include radially symmetric concentric phase profiles.

11. Method according to claim 10, characterized in that these concentric phase profiles are of the Laguerre-Gaussian, Bessel or "bottle beam" type.

12. Method according to claim 1, characterized in that the various spatial profiles include radially antisymmetric phase profiles.

13. Method according to claim 12, characterized in that these radially antisymmetric phase profiles are of the Hermite-Gaussian type.

14. Method according to claim 1, characterized in that a scanning with the excitation laser beam over or in the structured material is carried out.

15. Method according to claim 1, characterized in that the dimensional characteristics include at least one item from the following group: periodicity, distance, and angle.

16. Method according to claim 1, characterized in that different emission patterns are produced for different wavelengths.

17. System for the dimensional characterization of a structured material for implementing the method according to claim 1, this system comprising:
   - a laser source laser able to generate an excitation laser beam suitable for coherent nonlinear microscopy;
   - a spatial light modulator for modifying the spatial profile of the wavefront of the excitation laser beam into a non-Gaussian spatial profile;
   - a lens for focussing this excitation laser beam in a focal volume within the structured material;
   - a detector for detecting signals emitted by the structured material; and
   - a processing unit for producing a plurality of emission patterns each one corresponding to a particular shape of the focal volume; the particular shapes being obtained for different non-Gaussian spatial profiles of the wavefront of the excitation laser beam; and for deducing dimensional characteristics of said structured material from the emission patterns thus produced.

18. System according to claim 17, characterized in that the detector is arranged in such a way as to detect the signals backscattered by the structured material.

19. System according to claim 17, characterized in that the detector is arranged in such a way as to detect the transmission signals emerging downstream of the structured material.

20. System according to claim 17, characterized in that the detector is of the one-point type with or without a spatial filter.

21. System according to claim 17, characterized in that the detector is a camera.

22. System according to claim 17, characterized in that it comprises a scanning device for making the excitation laser beam scan over the structured material.

23. System according to claim 17, characterized in that the spatial light modulator is a device for the spatial shaping of the wavefront in phase.

24. System according to claim 23, characterized in that the modulator is a phase plate.

25. System according to claim 23, characterized in that the modulator is a liquid crystal matrix.

26. System according to claim 23, characterized in that the modulator is a deformable mirror.

27. System according to claim 17, characterized in that the spatial light modulator is a device for the spatial shaping of the wavefront in intensity.

* * * * *